US00PP23258P2

(12) United States Plant Patent
Francis

(10) Patent No.: US PP23,258 P2
(45) Date of Patent: Dec. 18, 2012

(54) ***LEUCADENDRON* PLANT NAMED 'EBONY'**

(50) Latin Name: *Leucadendron salignum×laureolum*
Varietal Denomination: Ebony

(76) Inventor: John Francis, Waimauku Auckland (NZ)

( * ) Notice: Subject to any disclaimer, the term of this patent is extended or adjusted under 35 U.S.C. 154(b) by 20 days.

(21) Appl. No.: 12/927,129

(22) Filed: Nov. 8, 2010

(51) Int. Cl.
*A01H 5/00* (2006.01)

(52) U.S. Cl. ..... Plt./226

(58) Field of Classification Search ..... Plt./226, Plt./263.1
See application file for complete search history.

*Primary Examiner* — June Hwu
(74) *Attorney, Agent, or Firm* — Mark P. Bourgeois

(57) ABSTRACT

A new cultivar of *Leucadendron* plant named 'Ebony' that is characterized by purple-black foliage, yellow flowers with purple-black bracts and an upright compact habit.

2 Drawing Sheets

Botanical classification: *Leucadendron salignum×laureolum.*

Variety denomination: 'Ebony'.

BACKGROUND OF THE INVENTION

The present invention relates to a new and distinct cultivar of *Leucadendron* plant botanically known as *Leucadendron salignum×laureolum* and hereinafter referred to by the cultivar name 'Ebony'.

'Ebony' is a naturally occurring branch mutation of *Leucadendron salignum×laureolum* 'Safari Sunset' (not patented). The new cultivar was discovered by the inventor in 2007 in a cultivated area of Waimauku Auckland, New Zealand. 'Ebony' was discovered in an outdoor field of 'Safari Sunset' cultivars being grown for cut foliage.

Asexual reproduction of the new cultivar 'Ebony' by terminal cuttings was first performed in 2007 in Waimauku Auckland, New Zealand. Since that time, under careful observation, the unique characteristics of the new cultivar have been uniform, stable and reproduced true to type in successive generations of asexual reproduction.

SUMMARY OF THE INVENTION

The following represent the distinguishing characteristics of the new *Leucadendron* cultivar 'Ebony'. These traits in combination distinguish 'Ebony' as a new and distinct cultivar.

1. *Leucadendron* 'Ebony' exhibits purple-black foliage.
2. *Leucadendron* 'Ebony' exhibits yellow flowers with purple-black bracts.
3. *Leucadendron* 'Ebony' exhibits an upright compact habit.

The closest comparison varieties are the parent plant *Leucadendron* 'Safari Sunset' and *Leucadendron* 'Goldstrike' (not patented).

The new cultivar 'Ebony' is distinguishable from the parent plant 'Safari Sunset' by the following characteristics: 'Ebony' has purple-black leaves. The leaves of 'Safari Sunset' are green. 'Ebony' has yellow flowers with purple-black bracts. The flowers of 'Safari Sunset' are yellow with red bracts. 'Ebony' has a more compact habit and is slower growing than 'Safari Sunset'.

The new cultivar 'Ebony' is distinguishable from 'Goldstrike' by the following characteristics: 'Ebony' has purple-black leaves. The leaves of 'Goldstrike' are green. 'Ebony' has yellow flowers with purple-black bracts. The flowers of 'Goldstrike' are yellow with yellow bracts.

BRIEF DESCRIPTION OF THE DRAWING

The accompanying photograph illustrates the distinguishing traits of *Leucadendron* 'Ebony'.

The plant in the photograph on sheet 1 shows an overall view of a 30 month old plant.

The photograph on sheet 2 illustrates an enlarged view of the flower. The photograph was taken using conventional techniques and although colors may appear different from actual colors due to light reflectance it is as accurate as possible by conventional photographic techniques.

BOTANICAL DESCRIPTION OF THE PLANT

The following is a detailed description of the new *Leucadendron* cultivar named 'Ebony'. Data was collected in Waimauku Auckland, New Zealand from 30 month old field grown plants. The time of year was Summer and the average temperature was 20 to 30° Centigrade during the day and 9 to 18° Centigrade at night. Color determinations are in accordance with The Royal Horticultural Society Colour Chart 2007 edition, except where general color terms of ordinary dictionary significance are used. The growing requirements are similar to the species. 'Ebony' has not been tested under all possible conditions and phenotypic differences may be observed with variations in environmental, climatic, and cultural conditions, however, without any variance in genotype.

Botanical classification: *Leucadendron salignum×laureolum* 'Ebony'.

Use: Ornamental Perennial.

Parentage: 'Ebony' is a naturally occurring branch mutation of *Leucadendron salignum×laureolum* 'Safari Sunset'.

Vigor: Moderate.

Container size: 3 to 6 liter pots.

Growth habit: Upright.
Plant shape: Ovate.
Height: Average 2.0 m. in height.
Width: Average 1.5 m. in width.
Hardiness: −9° to 38° C.
Propagation: Terminal cuttings.
Crop time: 15 months.
Stem:
*Branching habit*.—Free branching.
*Number of lateral branches*.—Approximately 22.
*Lateral branch diameter*.—30 mm. in diameter.
*Lateral branch length*.—1.0 m. in length.
*Lateral branch strength*.—Strong.
*Color*.—187A.
*Pubescence*.—Absent.
*Internode length*.—3 cm. between nodes.
*Shape*.—Round.
Foliage:
*Leaf arrangement*.—Opposite.
*Compound or single*.—Single.
*Leaf shape*.—Oblanceolate.
*Leaf apex*.—Acute.
*Leaf base*.—Attenuate.
*Leaf length*.—8.0 cm. in length.
*Leaf width*.—1.5 cm. in width.
*Texture*.—Smooth both surfaces.
*Pubescence*.—Absent.
*Leaf margin*.—Entire.
*Young leaf color* (*upper surface*).—203D.
*Young leaf color* (*lower surface*).—203D.
*Mature leaf color* (*upper surface*).—203D.
*Mature leaf color* (*lower surface*).—203D.
*Fall leaf color* (*upper surface*).—147A with midrib N186C.
*Fall leaf color* (*lower surface*).—147A with midrib N186C.
*Leaf attachment*.—Sessile.
Flower:
*Flower arrangement*.—Female flowers only arranged on an ovate spike.
*Inflorescence dimensions*.—2.0 cm. in length and 1.2 cm. in diameter.
*Quantity of flowers and buds per inflorescence*.—Approximately 80.
*Flowering season*.—Summer.
*Fragrance*.—None.
*Self-cleaning or persistent*.—Self cleaning.
*Flower bud length*.—0.5 mm. in length.
*Flower bud diameter*.—0.5 mm. in diameter.
*Flower bud shape*.—Ovate.
*Bud color*.—N138C.
*Number of floret masses per flower head*.—One.
*Floret mass dimensions*.—2.0 cm. in length and 1.2 cm in diameter.
*Flower aspect*.—Outward.
*Flower dimensions*.—2 mm. in diameter and 2 mm. in height.
*Flower longevity*.—Lasts approximately 3 weeks.
*Petal arrangement*.—Four fused into a tube.
*Petal shape*.—Obovate.
*Petal margin*.—Entire.
*Petal apex*.—Rounded.
*Petal texture*.—Smooth both surfaces.
*Petal dimensions*.—2 mm. in length and 0.5 mm. in width.
*Petal color when opening* (*upper side*).—9B.
*Petal color when opening* (*under side*).—9B.
*Petal color when fully opened* (*upper side*).—9B.
*Petal color when fully opened* (*under side*).—9B.
*Floret basal bract dimensions*.—1.5 mm. in length and 0.5 mm in width.
*Floret basal bract color* (*upper side*).—N199C.
*Floret basal bract color* (*under side*).—N199C.
Involucular bracts:
*Bract number*.—8.
*Bract shape*.—Oblanceolate.
*Bract margin*.—Entire.
*Bract apex*.—Acute.
*Bract base*.—Attenuate.
*Bract texture*.—Smooth both surfaces.
*Bract dimensions*.—8 cm. in length and 1.5 cm. in width.
*Bract color when opening* (*upper side*).—187A.
*Bract color when opening* (*under side*).—187A.
*Bract color when fully opened* (*upper side*).—187A.
*Bract color when fully opened* (*under side*).—187A.
Sepals: Absent.
Peduncle:
*Peduncle length*.—40 cm.
*Peduncle strength*.—Moderate.
*Peduncle texture*.—Smooth.
*Peduncle color*.—59B.
Reproductive organ (female):
*Pistil*.—Quantity: One. Length: 6 mm. Stigma shape: heart shaped. Stigma color: 15B. Style length: 4.5 mm. Style color: 45C. Ovary color: 141B.
Fruit and seed production: Plants of the new *Leucadendron* have not been observed for fruit and seed production.
Disease and pest resistance: Plants of the new *Leucadendron* have not been observed for disease or pest resistance.

The invention claimed is:

1. A new and distinct variety of *Leucadendron* plant named 'Ebony' as described and illustrated.

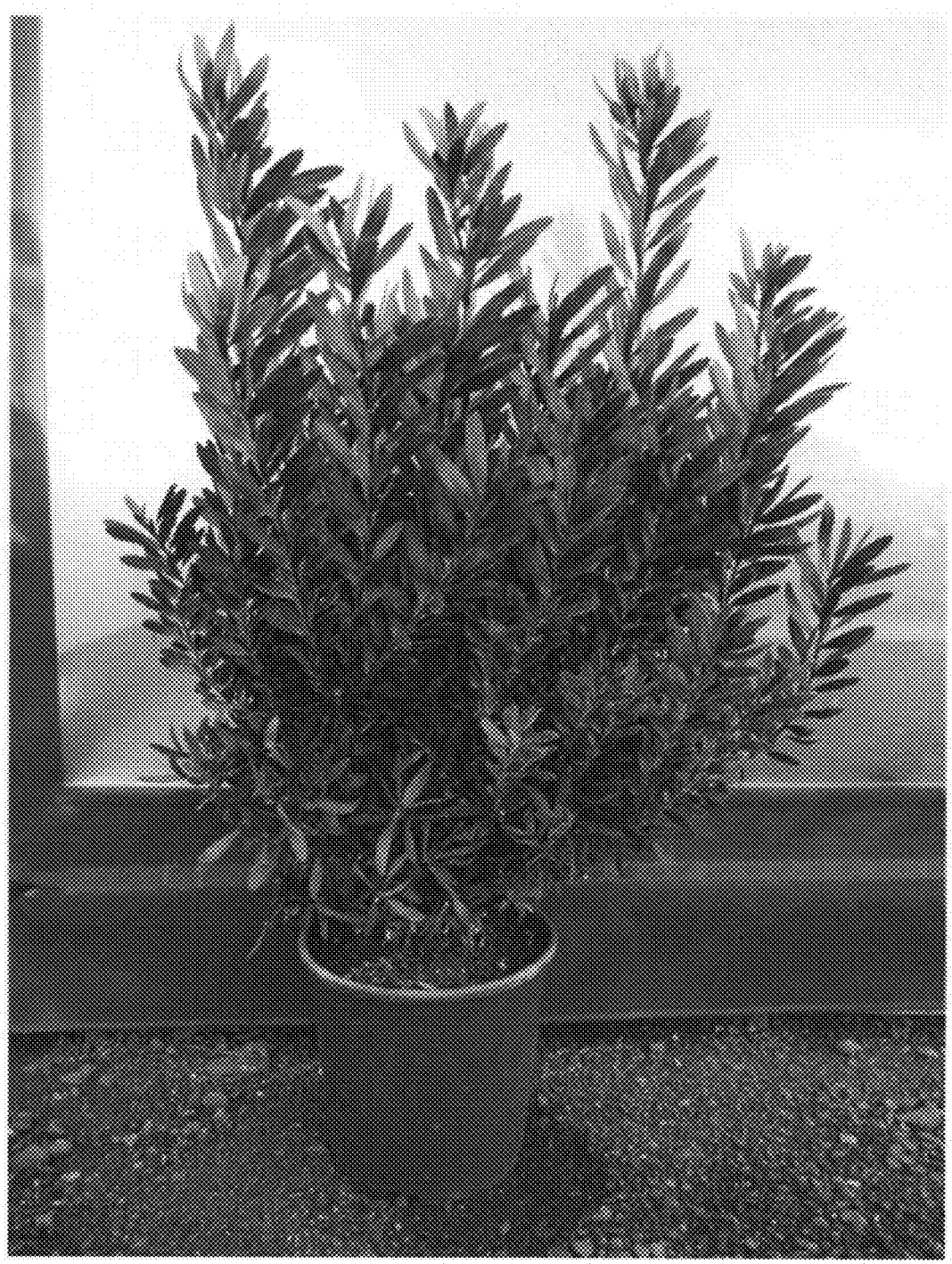

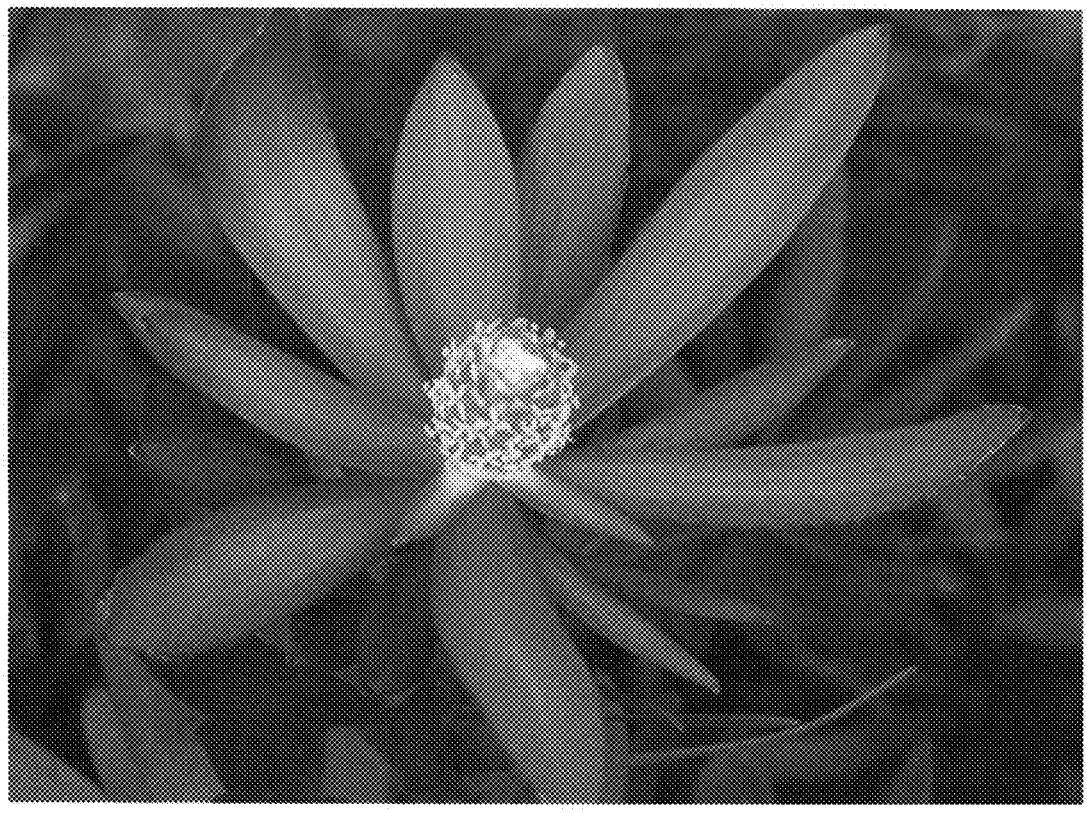

* * * * *